US010820906B2

(12) United States Patent
Brandeis

(10) Patent No.: US 10,820,906 B2
(45) Date of Patent: Nov. 3, 2020

(54) BIODEGRADABLE BLOOD VESSEL OCCLUSION AND NARROWING

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

(*) Notice: Subject to any disclaimer, the term of this patent is extended or adjusted under 35 U.S.C. 154(b) by 203 days.

(21) Appl. No.: 15/813,356

(22) Filed: Nov. 15, 2017

(65) Prior Publication Data

US 2018/0070953 A1 Mar. 15, 2018

Related U.S. Application Data

(63) Continuation of application No. 14/411,389, filed as application No. PCT/IL2013/050538 on Jun. 25, 2013, now abandoned.

(60) Provisional application No. 61/722,826, filed on Nov. 6, 2012, provisional application No. 61/664,222, filed on Jun. 26, 2012.

(51) Int. Cl.
| | | |
|---|---|---|
| A61B 17/12 | (2006.01) | |
| A61B 17/00 | (2006.01) | |
| A61B 17/064 | (2006.01) | |
| A61F 2/01 | (2006.01) | |
| A61B 17/221 | (2006.01) | |

(52) U.S. Cl.
CPC .. *A61B 17/12109* (2013.01); *A61B 17/00491* (2013.01); *A61B 17/064* (2013.01); *A61B 17/1204* (2013.01); *A61B 17/1214* (2013.01); *A61B 17/12036* (2013.01); *A61B 17/12131* (2013.01); *A61B 17/12172* (2013.01); *A61F 2/01* (2013.01); *A61B 2017/00004* (2013.01); *A61B 2017/00867* (2013.01); *A61B 2017/0641* (2013.01); *A61B 2017/1205* (2013.01); *A61B 2017/2215* (2013.01); *A61F 2002/016* (2013.01)

(58) Field of Classification Search
None
See application file for complete search history.

(56) References Cited

U.S. PATENT DOCUMENTS

| | | |
|---|---|---|
| 5,527,338 A | 6/1996 | Purdy |
| 6,048,331 A | 4/2000 | Tsugita et al. |
| 6,117,157 A | 9/2000 | Tekulve |
| 6,267,776 B1 | 7/2001 | O'Connell |
| 6,273,901 B1 | 8/2001 | Whitcher et al. |
| 6,419,686 B1 | 7/2002 | McLeod et al. |

(Continued)

FOREIGN PATENT DOCUMENTS

| | | |
|---|---|---|
| CN | 101612052 | 12/2009 |
| DE | 233303 | 2/1986 |

(Continued)

OTHER PUBLICATIONS

Communication Pursuant to Article 94(3) EPC dated May 11, 2017 From the European Patent Office Re. Application No. 13810252.0. (5 Pages).

(Continued)

*Primary Examiner* — Shaun L David

(57) ABSTRACT

A biodegradable blood vessel narrowing device, comprising: a biodegradable element; an anchoring element; wherein said anchoring element is anchored to a blood vessel wall and at least one external dimension of said biodegradable element is reduced upon biodegradation of said biodegradable element thereby pulling said blood vessel walls toward one another.

13 Claims, 8 Drawing Sheets

(56) References Cited

U.S. PATENT DOCUMENTS

| | | |
|---|---|---|
| 8,029,529 B1 | 10/2011 | Chanduszko |
| 2002/0090389 A1 | 7/2002 | Humes et al. |
| 2003/0195514 A1 | 10/2003 | Trieu et al. |
| 2003/0208227 A1 | 11/2003 | Thomas |
| 2004/0034366 A1 | 2/2004 | Van der Burg et al. |
| 2005/0107822 A1 | 3/2005 | WasDyke |
| 2005/0159771 A1 | 7/2005 | Petersen |
| 2006/0015144 A1 | 1/2006 | Burbank et al. |
| 2006/0058833 A1 | 3/2006 | VanCamp et al. |
| 2006/0287674 A1 | 12/2006 | Ginn et al. |
| 2007/0129753 A1 | 6/2007 | Quinn et al. |
| 2007/0173885 A1 | 7/2007 | Cartier et al. |
| 2008/0045996 A1 | 2/2008 | Makower et al. |
| 2008/0188887 A1 | 8/2008 | Batiste |
| 2008/0210738 A1 | 9/2008 | Shelton et al. |
| 2008/0221599 A1 | 9/2008 | Starksen |
| 2009/0062838 A1 | 3/2009 | Brumleve et al. |
| 2009/0216261 A1 | 8/2009 | Brandeis et al. |
| 2009/0228038 A1 | 9/2009 | Amin |
| 2009/0306703 A1 | 12/2009 | Kashkarov et al. |
| 2010/0016881 A1 | 1/2010 | Fleck et al. |
| 2010/0163054 A1 | 7/2010 | Brenzel et al. |
| 2011/0196468 A1 | 8/2011 | Brandeis |
| 2011/0213404 A1 | 9/2011 | Binkert |
| 2011/0301630 A1 | 12/2011 | Hendriksen et al. |
| 2012/0179172 A1 | 7/2012 | Paul, Jr. et al. |
| 2013/0006294 A1 | 1/2013 | Kashkarov et al. |
| 2015/0142025 A1 | 5/2015 | Brandeis |
| 2015/0190140 A1 | 7/2015 | Brandeis |
| 2016/0157986 A1 | 6/2016 | Brandeis |

FOREIGN PATENT DOCUMENTS

| | | |
|---|---|---|
| DE | 102009058132 | 6/2011 |
| EP | 1276437 | 1/2003 |
| EP | 1878391 | 1/2008 |
| WO | WO 99/07292 | 2/1999 |
| WO | WO 01/72239 | 10/2001 |
| WO | WO 03/020106 | 3/2003 |
| WO | WO 03/079944 | 10/2003 |
| WO | WO 2006/017470 | 2/2006 |
| WO | WO 2008/115922 | 9/2008 |
| WO | WO 2010/022072 | 2/2010 |
| WO | WO 2011/037866 | 3/2011 |
| WO | WO 2014/002087 | 1/2014 |
| WO | WO 2014/002088 | 1/2014 |

OTHER PUBLICATIONS

Communication Pursuant to Article 94(3) EPC dated Dec. 19, 2016 From the European Patent Office Re. Application No. 13810252.0. (5 Pages).

Communication Pursuant to Rule 164(1) EPC [Supplementary Partial European Search Report] dated Feb. 5, 2016 From the European Patent Office Re. Application No. 13809443.8.

International Preliminary Report on Patentability dated Jan. 8, 2015 From the International Bureau of WIPO Re. Application No. PCT/IL2013/050537.

International Preliminary Report on Patentability dated Jan. 8, 2015 From the International Bureau of WIPO Re. Application No. PCT/IL2013/050538.

International Search Report and the Written Opinion dated Oct. 15, 2013 From the International Searching Authority Re. Application No. PCT/IL2013/050538.

International Search Report and the Written Opinion dated Oct. 29, 2013 From the International Searching Authority Re. Application No. PCT/IL2013/050537.

Invitation to Pay Additional Fees dated Sep. 8, 2013 From the International Searching Authority Re. Application No. PCT/IL2013/050537.

Official Action dated Aug. 13, 2015 From the US Patent and Trademark Office Re. U.S. Appl. No. 14/411,388.

Official Action dated Jun. 15, 2017 From the US Patent and Trademark Office Re. U.S. Appl. No. 14/411,389. (33 Pages).

Restriction Official Action dated Jun. 2, 2015 From the US Patent and Trademark Office Re. U.S. Appl. No. 14/411,388.

Restriction Official Action dated Feb. 13, 2017 From the US Patent and Trademark Office Re. U.S. Appl. No. 14/411,389. (10 pages).

Supplementary European Search Report and the European Search Opinion dated Feb. 9, 2016 From the European Patent Office Re. Application No. 13810252.0.

Supplementary European Search Report and the European Search Opinion dated Jun. 20, 2016 From the European Patent Office Re. Application No. 13809443.8.

Examiner-Initiated Interview Summary dated Oct. 22, 2018 From the US Patent and Trademark Office Re. U.S. Appl. No. 15/044,141. (4 pages).

Official Action dated Jan. 23, 2019 From the US Patent and Trademark Office Re. U.S. Appl. No. 15/044,141. (26 pages).

Restriction Official Action dated May 4, 2018 From the US Patent and Trademark Office Re. U.S. Appl. No. 15/044,141. (10 pages).

Official Action dated Aug. 5, 2019 From the US Patent and Trademark Office Re. U.S. Appl. No. 15/044,141. (10 pages).

Advisory Action Before the Filing of an Appeal Brief dated Dec. 19, 2019 From the US Patent and Trademark Office Re. U.S. Appl. No. 15/044,141. (4 pages).

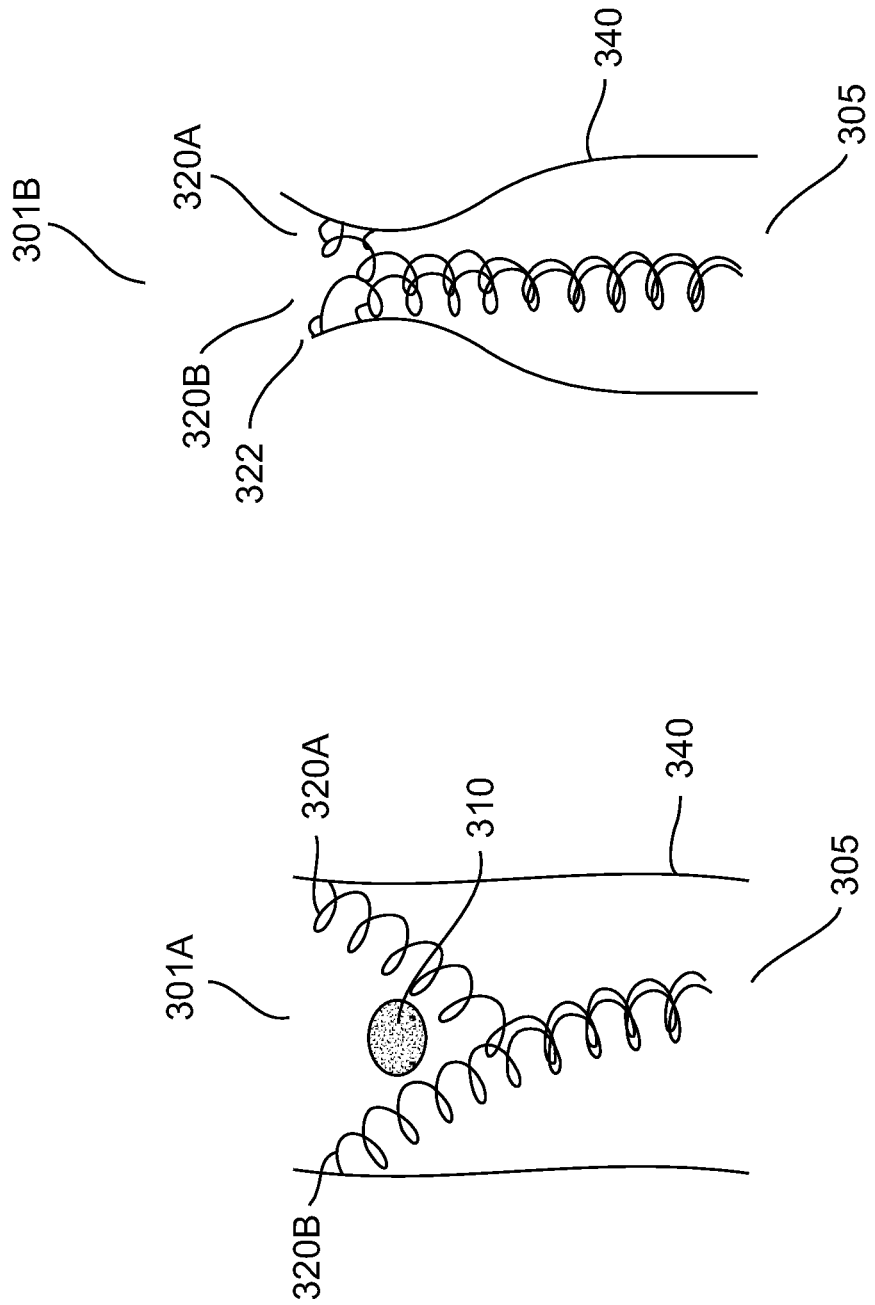

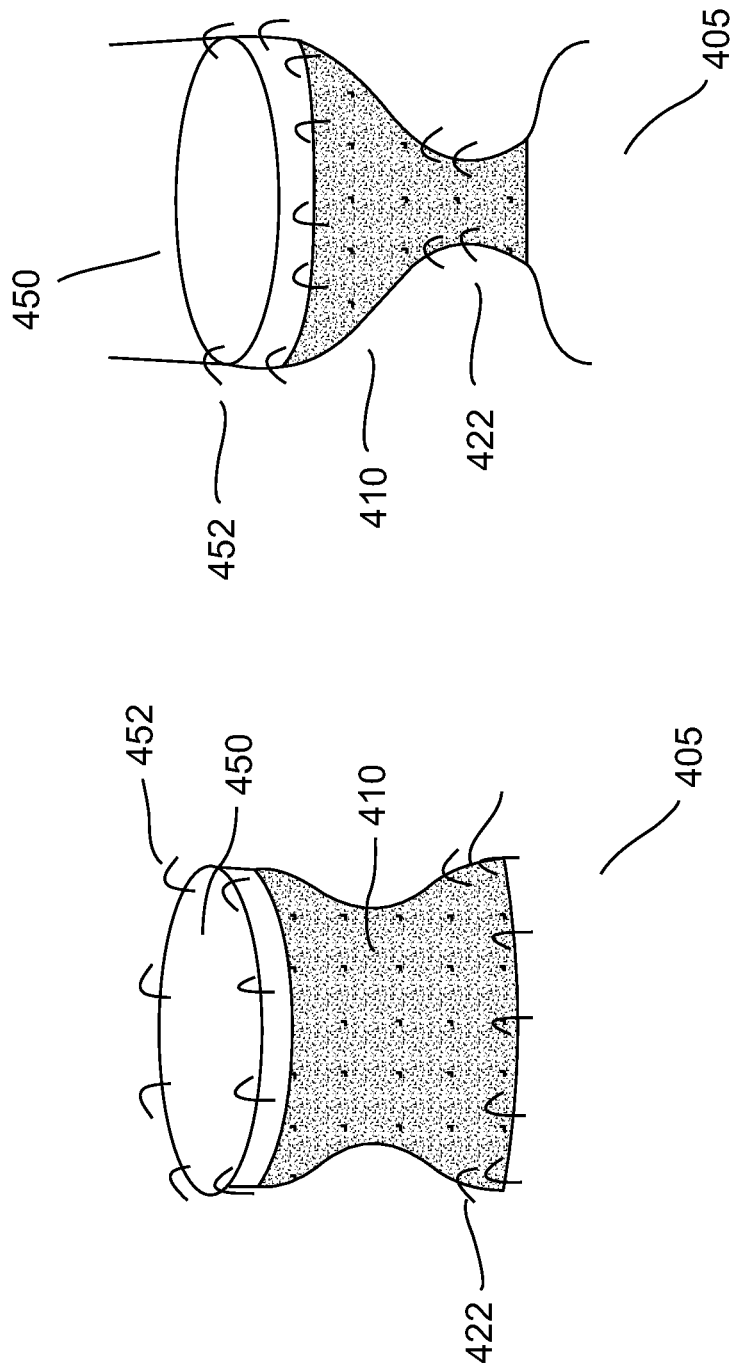

FIG. 6A
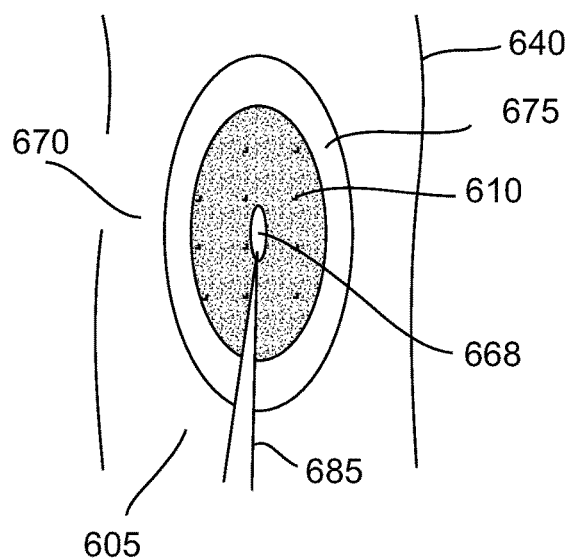
FIG. 6B
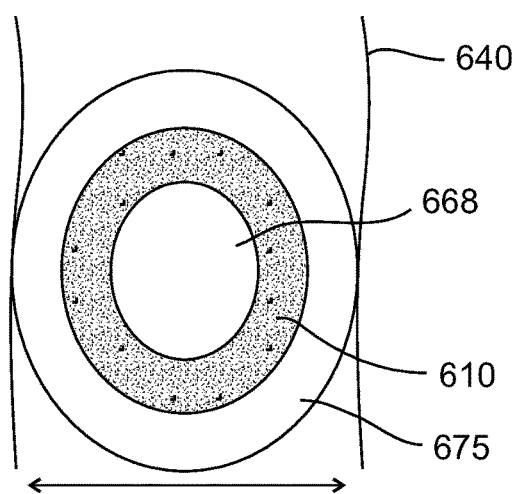
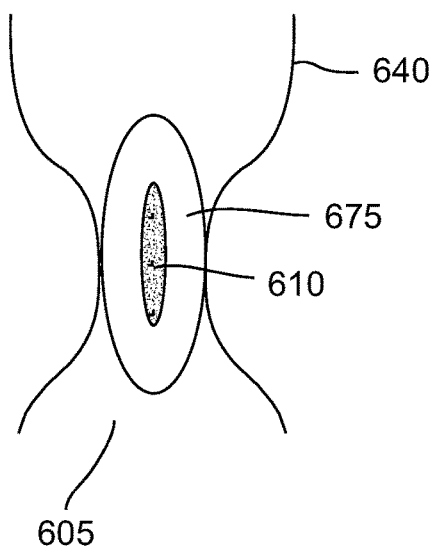
FIG. 6C

BIODEGRADABLE BLOOD VESSEL OCCLUSION AND NARROWING

RELATED APPLICATIONS

This application is a continuation of U.S. patent application Ser. No. 14/411,389 filed on Dec. 25, 2014, which is a National Phase of PCT Patent Application No. PCT/IL2013/050538 having International Filing Date of Jun. 25, 2013, which claims the benefit of priority under 35 USC § 119(e) of U.S. Provisional Patent Application Nos. 61/664,222 filed on Jun. 26, 2012 and 61/722,826 filed on Nov. 6, 2012. The contents of the above applications are all incorporated by reference as if fully set forth herein in their entirety.

FIELD AND BACKGROUND OF THE INVENTION

The present invention, in some embodiments thereof, relates to blood vessel treatment and, more particularly, but not exclusively, to biodegradable devices and/or methods for blood vessel occlusion and narrowing.

A malfunction in the ability of veins or arteries to supply or remove blood is associated with medical conditions such as varicose vein expansion, aneurisms, tumors, trauma and dissection of blood vessels.

Varicose veins appear in 20-25% of women and 10-15% of men. Most varicose veins are considered a cosmetic condition rather than a medical condition; however, in some cases, hindered circulation may cause pain, disfiguring, swelling, discomfort, a tingling sensation, itching and/or a feeling of heaviness.

Several techniques and procedures to treat varicose veins exist. Vein stripping involves tying off of the upper end of a vein and then removing the vein. Vein stripping is typically performed in an operating room under general anesthesia. Approximately 150,000 vein stripping surgeries are performed each year in the U.S. Vein stripping associated risks include risks linked to general anesthesia such as anesthesia allergies, infections etc. In addition, tissue around the stripped vein may become bruised and scarred causing a feeling of "tightness" in the leg. Damaged may cause numbness and paralysis of part of the leg.

Endovenous laser treatment is typically performed done in-office under local anesthesia. Endovenous laser treatment uses intense heat to remove a vein, which may lead to an increased risk of developing blood clots. Treated veins can also become irritated and inflamed, leading to pain and swelling in the legs. The treated area can begin to tingle or become burned from the heat.

Radiofrequency occlusion is typically performed done in-office under local anesthesia or in an ambulatory surgery setting. A small tube or catheter is used and threaded along the vein using ultrasound guidance. Local anesthetic is injected along the way to help ensure the patient's comfort throughout the procedure. Once the vein is canalized, sound waves are applied to heat and collapse the vein from the top, down. The vein will eventually result in a thin scar tissue and is absorbed by the body's natural processes. Following treatment with radiofrequency occlusion, a compression bandage is applied to the leg to aid in the healing process. This should be kept in place for a couple of days and then compression stockings are worn for another two to three weeks to continue to aid the healing process. Patients may walk shortly after treatment and most are able to resume normal activities or return to work after a few days provided they avoid heavy lifting and wear their compression stockings. There may be a chance of bleeding, infection or blood clots with radiofrequency occlusion as with many other procedures. A unique complication that is associated with radiofrequency occlusion, however, is skin burn due to the method of occlusion used during treatment.

Ultrasound-guided sclerotherapy is typically performed done in-office under local anesthesia. Side effects that are applicable for standard sclerotherapy are also applicable to ultrasound-guided sclerotherapy, although the magnitude of certain complications, when they occur, may be greater. Standard sclerotherapy side effects include skin ulceration or necrosis, deep vein thrombosis, allergic reaction, arterial injection, pulmonary embolus, nerve injury, wound breakdown and wound inflammation.

The artificial blocking of blood flow is known generically as "embolization" and/or "occlusion". The embolization of a vessel in an organ may be used to treat a variety of maladies; typically though, embolization is used.

SUMMARY OF THE INVENTION

According to an aspect of some embodiments of the present invention there is provided a biodegradable blood vessel narrowing device, comprising: a biodegradable element; an anchoring element sized and shaped to be anchored to a blood vessel wall when located in a blood vessel lumen; and at least one external dimension of the biodegradable element is reduced upon biodegradation of the biodegradable element thereby pulling the blood vessel walls toward one another. Optionally, the device occludes a blood vessel upon the device deployment in the blood vessel. Optionally, the device partially occludes a blood vessel upon the device deployment in the blood vessel. Optionally, the anchoring element is made of a shape memory alloy (SMA). Optionally, the anchoring element is made of a biocompatible polymer. Optionally, a degradation of the biodegradable element is initiated by external degradation means. Optionally, the anchoring element comprises a plurality of anchoring legs, each the anchoring leg having at least one anchoring tooth for anchoring to a blood vessel wall and a distance between at least two of respective the anchoring teeth shortens upon biodegradation of the biodegradable element. Optionally, the plurality of anchoring legs essentially encircles the biodegradable element. Optionally, the device further comprises a constriction element wherein the constriction element and upon biodegradation of the biodegradable element the constriction element applies pressure on the plurality of anchoring legs thereby bringing the plurality of anchoring legs to a closer proximity to one another. Optionally, the device further comprises a constriction element wherein the constriction element encircles the plurality of anchoring legs and the biodegradable element is positioned essentially inside the constriction element and upon biodegradation of the biodegradable element the constriction element applies pressure on the plurality of anchoring legs thereby pulling the plurality of anchoring legs. Optionally, the biodegradable element being positioned between at least one of the anchoring legs and a part of the device which is adjacent to at least one of the anchoring legs and upon degradation of the biodegradable element the distance between the at least one of the anchoring legs and the part. Optionally, the anchoring leg has a first leg part and a second leg part carrying the at least one anchoring tooth, the biodegradable element being positioned between the first leg part and the second leg part and upon degradation of the biodegradable element the distance between the first part and the second part shortens. Optionally, the biodegradable element encircles the plurality of anchoring legs thereby fastening the plurality of anchoring legs and a distance between the plurality of anchoring legs after degradation of the biodegradable element is shorter than a distance between the plurality of anchoring legs prior to degradation of the biodegradable element. Optionally, each of the plurality of anchoring legs further comprise a retention element and the plurality of anchoring legs have a twisted state in which the plurality of anchoring legs are twisted around one another and an untwisted state and a distance between the plurality of anchoring legs in the twisted state is bigger than a distance between the plurality of anchoring legs in the untwisted state and the biodegradable element encircles the plurality of anchoring legs in their twisted state thereby fastening the plurality of anchoring legs and the retention element restricts the movement of the biodegradable element and upon degradation of the biodegradable element the plurality of anchoring legs switch from a the twisted state to the untwisted state. Optionally, each of the plurality of anchoring legs is a spring shaped element. Optionally, the device further comprises an internal chamber wherein the device is capsule shaped and filling of the internal chamber enlarges an external dimension of the device to fit a blood vessel. Optionally, the biodegradable blood vessel narrowing device has an outer surface and the anchoring element comprises: a glue chamber internal to the capsule; a plurality of glue channels connecting the chamber to the capsule surface; and a bio-compatible glue; wherein the biocompatible glue flows from the glue chamber to the outer surface through the plurality of glue channels thereby gluing the biodegradable blood vessel narrowing device to a vessel wall. Optionally, the device further comprises a layer and the layer is positioned external to the glue chamber and internal to biodegradable element and upon degradation of the biodegradable element the layer applies pressure on the glue chamber thereby inserting the bio-compatible glue into the plurality of glue channels. Optionally, the device further comprises: a chamber internal to the biodegradable blood vessel narrowing device; a channel connecting the chamber to a surface of the capsule; wherein the channel transfers a bio-absorbable material between the chamber and an exterior of the capsule. Optionally, the device further comprises an occlusion element, wherein the occlusion element occludes a blood vessel.

According to an aspect of some embodiments of the present invention there is provided a method for occluding and narrowing a blood vessel, comprising: deploying a biodegradable blood vessel narrowing device in a blood vessel; and attaching an anchoring element of the biodegradable blood vessel narrowing device to walls of the blood vessel; wherein narrowing of the blood vessel is mechanically linked to biodegradation of the biodegradable blood vessel narrowing device. Optionally, the method of further comprises applying external degradation means to the device for initiating biodegradation. Optionally, the method further comprises filling a chamber in the device with a bio-absorbable material. Optionally, the attachment of an anchoring element is performed by releasing bio-compatible glue from the biodegradable blood vessel narrowing device and gluing of the biodegradable blood vessel narrowing device to a blood vessel wall. Optionally, the method further comprises filling a glue chamber in the biodegradable blood vessel narrowing device with bio-compatible glue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A is an illustration of a biodegradable blood vessel narrowing device with spring shaped anchoring legs spaced by a biodegradable element in a pre-degradation state, according to some embodiments of the present invention;

FIG. 3B is an illustration of a biodegradable blood vessel narrowing device with spring shaped anchoring legs spaced by a biodegradable element in a degraded state, according to some embodiments of the present invention;

FIG. 4A is an illustration of a biodegradable blood vessel narrowing device with an occlusion element in a pre-degradation state, according to some embodiments of the present invention;

FIG. 4B is an illustration of a biodegradable blood vessel narrowing device with an occlusion element in a degraded state, according to some embodiments of the present invention;

FIG. 6A is an illustration of a biodegradable blood vessel narrowing device with an empty internal chamber and a channel in a pre-degradation state, according to some embodiments of the present invention;

FIG. 6B is an illustration of a biodegradable blood vessel narrowing device with a filled internal chamber and a channel in a pre-degradation state, according to some embodiments of the present invention;

FIG. 6C is an illustration of a biodegradable blood vessel narrowing device with a filled internal chamber and a channel in a degraded state, according to some embodiments of the present invention;

DESCRIPTION OF SPECIFIC EMBODIMENTS OF THE INVENTION

Figure 1A:
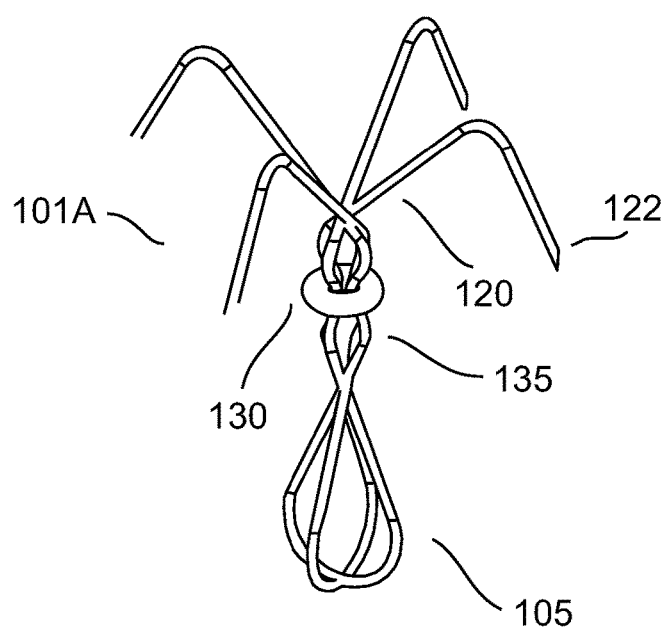
FIG. 1A is an illustration of a biodegradable blood vessel narrowing device with multiple anchoring legs in a twisted state, according to some embodiments of the present invention.

The present invention, in some embodiments thereof, relates to devices and methods for blood vessel occlusion and narrowing and, more particularly, but not exclusively, to biodegradable blood vessel narrowing devices and methods for occluding and narrowing a blood vessel using a biodegradable element.

According to some embodiments of the present invention, there are provided a biodegradable blood vessel narrowing devices which anchor to a blood vessel wall and narrow the blood vessel upon a degradation of its biodegradable element. Such a biodegradable blood vessel narrowing device has a biodegradable scaffold or block, referred to herein as a biodegradable element and one or more anchoring elements for anchoring the biodegradable blood vessel narrowing device to the blood wall. For brevity, the one or more anchoring elements are referred to herein as an anchoring element. The anchoring element includes one or more anchoring legs, hooks and/or biocompatible glue. The anchoring element may be made of a shape memory alloy (SMA). Upon degradation of the biodegradable element the blood vessel the anchoring element changes its formation to pull the blood vessel walls inwardly, thereby narrowing the blood vessel. The anchored biodegradable blood vessel narrowing device is set to occlude the blood vessel completely and/or partially, immediately and/or overtime. Occlusion may be performed by an occlusion element that attaches to the blood vessel independently of the biodegradable blood vessel narrowing device and/or is attached to the biodegradable blood vessel narrowing device.

Variations of the blood vessel narrowing device achieve the blood vessel narrowing with different configurations. The device may have anchoring legs, be capsule shaped, tube shaped and/or have anchoring springs. The biodegradable elements shape, number, position and/or relation with the anchoring element may differ between these variations. For example, the biodegradable element may include one or more biodegradable ring encircling anchoring legs. The anchoring legs are twisted around one another and are held in that state by the biodegradable ring. A retention element secures the ring in place and prevents and/or limits its movement. Upon degradation of the biodegradable ring the anchoring legs switch from twisted open state to an untwisted closed state. The legs are closer to each other in the untwisted closed state. With their movement towards one another the anchoring legs pull with them the blood vessel wall and narrow the blood vessel.

A blood vessel narrowing device is inserted into a blood vessel in a state that fits the blood vessel shape and dimensions. The blood vessel narrowing device is then deployed in the blood vessel. The anchoring element attaches to the blood vessel walls. The attachment may be performed using biocompatible glue. When a bio-absorbable material is used it is first inserted into an internal chamber of the device. The insertion of the bio-absorbable material may bring the anchoring element into a position that allows its attachment to the blood vessel walls. Then the insertion means, for example a capillary, may be removed.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIGS. 1A-6C illustrate variations of a biodegradable blood vessel narrowing device 105, 205, 305, 405, 605. FIGS. 1A, 2A, 3A, 4A, 5A and 6A illustrate a pre-degradation state with the biodegradable element 110 and/or the constriction element 130 not yet degraded. FIGS. 1B, 2B, 3B, 4B, 5B and 6C illustrate a degraded state with the biodegradable element 110 and/or the constriction element 130 partially and/or fully degraded.

Figure 1B:
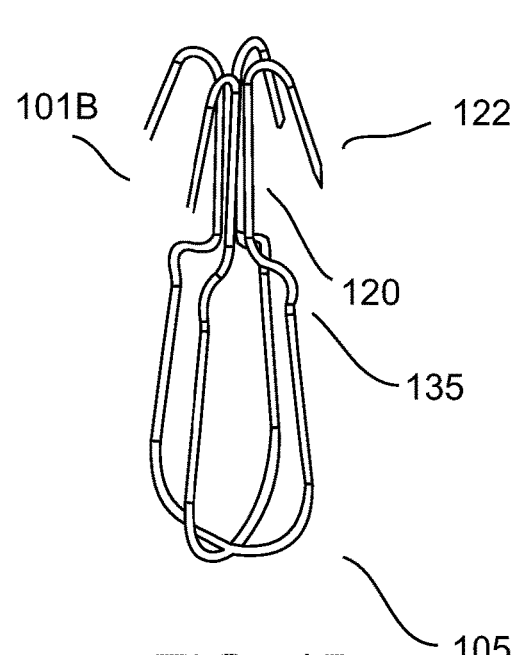
FIG. 1B is an illustration of a biodegradable blood vessel narrowing device with multiple anchoring legs in an untwisted state, according to some embodiments of the present invention.
Figure 8:
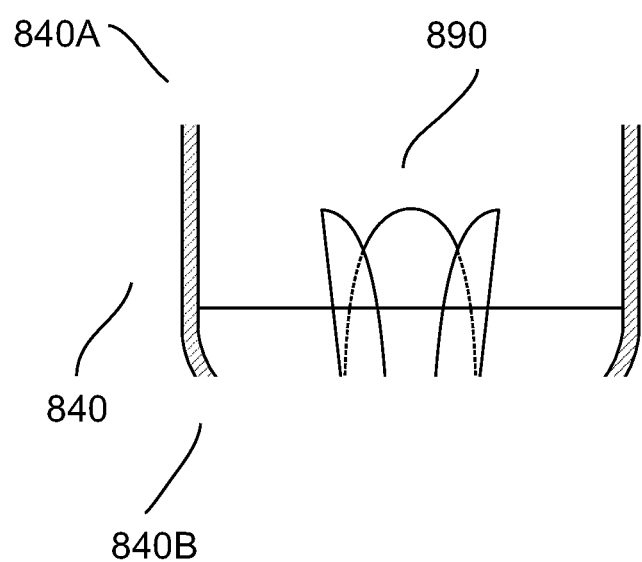
FIG. 8 is an illustration of a blood clot cage, according to some embodiments of the present invention.

FIGS. 1A and 1B illustrate a biodegradable blood vessel narrowing device 105 with multiple anchoring legs 120 in a twisted state 101A and untwisted state 101B, according to some embodiments of the present invention. The biodegradable blood vessel narrowing device 105 has multiple anchoring legs 120. In these examples four anchoring legs 120 are depicted. The anchoring legs 120 have sharp teeth 122 used for anchoring the device 105 to a blood vessel wall. Optionally, the anchoring legs 120 are made of an SMA such as copper-aluminium-nickel, nickel-titanium, zinc alloy, copper alloy, gold alloy and/or iron alloy. When the anchoring legs 120 are twisted, as in FIG. 1A, they are spread apart to touch opposing sides of a blood vessel wall. The twisted state 101A is maintained by a biodegradable constriction element 130. In this example the biodegradable constriction element is a loop which encircles the anchoring legs 120. Such a constriction element 130 is held in its position by one or more retention elements 135 on one or more of the anchoring legs 120, for example segments of the anchoring legs 120. Here, the retention element 135 is shaped as an arch. The constriction element 130 is made of a biodegradable material. As used herein, biodegradable material means a biodegradable, bio-absorbable and/or re-absorbable material for internal use, of a synthetic and/or natural source which can be degraded (i.e., broken down) and/or absorbed in a physiological environment such as by proteases. Biodegradability may depend on the availability of degradation substrates (i.e., biological materials or portion thereof which are part of the polymer), the presence of biodegrading materials (e.g., microorganisms, enzymes, proteins) and the availability of oxygen, carbon dioxide and/or other nutrients (for aerobic organisms, microorganisms and/or portions thereof). Examples of biodegradable material include, but are not limited to: a polyglycolic acid (PGA), Maxon-PGA, Tri-Methylene Carbonate (TMC), Vicryl PGA, Vicryl Polylactide, polylactic acid (PLA), polyglycolic acid (PLGA), Dexon olyglycolide, polycaprolactone (PCL), polydioxanone (PDO), Polydioxanone (PDS), polyethyleneglycol (PEG), PEG-DMA, Polyethylenimine (PEI), hyaluronic acid, catgut suture material, gelatin, cellulose, nitrocellulose, collagen, gelatin, albumin, fibrin, alginate, hydrogels, chitosan copolymers and/or other synthetic and naturally-occurring biodegradable materials and/or mixtures thereof. The biodegradable material may be a homo-polymer or a copolymer. When the biodegradable material of the constriction element degrades, the constriction element 135 is loosened and the anchoring legs 120 transfer from the twisted state 101A, as depicted in FIG. 1A, to the untwisted state 101B as depicted in FIG. 1B. Optionally, the change from the twisted state 101A to the untwisted state 101B is promoted by the shape memory of SMA anchoring legs 120: The SMA anchoring legs 120 tend to be essentially straight and close to one another as a result of their shape memory. Without external pressure and/or retention the SMA anchoring legs 120 tend to move to the untwisted state 101B. The anchoring legs 120 are closer to one another in the untwisted state 101B than in the twisted state 101A. Optionally the biodegradable blood vessel narrowing device 105 may have a blood clot cage 890 as illustrated in FIG. 8. The biodegradation may be gradual. Gradual biodegradation may achieve a gradual narrowing of a blood vessel. The biodegradable blood vessel narrowing device 105 may occlude the blood vessel immediately and completely upon insertion and/or deployment. Optionally, the biodegradable blood vessel narrowing device 105 in a twisted state 101A partially occludes the blood vessel upon insertion and/or deployment. Then, upon gradual transition to an untwisted state 101B the biodegradable blood vessel narrowing device 105 achieves a higher level of occlusion. Optionally, upon an essentially complete biodegradation of the constriction element 130, an essentially complete occlusion of the blood vessel is achieved by the biodegradable blood vessel narrowing device 105. Optionally, an accompanying occlusion device is used to achieve immediate occlusion and the biodegradable blood vessel narrowing device 105 narrows the blood vessel over time. Optionally, the accompanying occlusion device is removed when occlusion is achieved by the biodegradable blood vessel narrowing device 105.

Figure 1C:
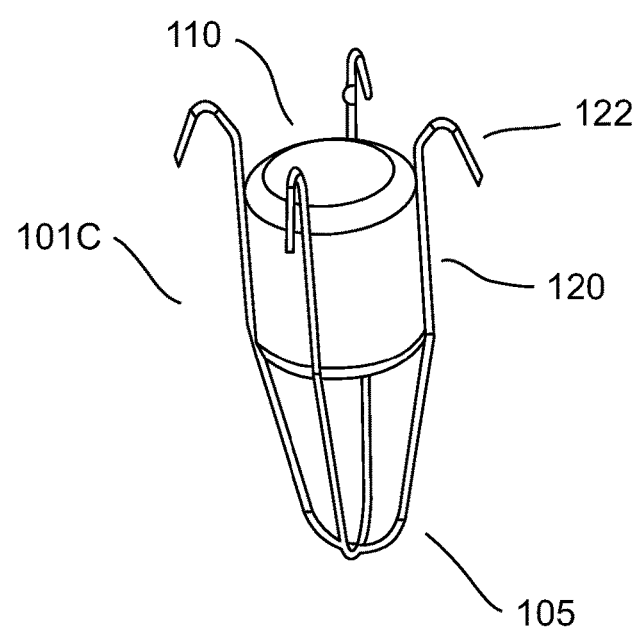
FIG. 1C is an illustration of a biodegradable blood vessel narrowing device with multiple anchoring legs in an open state, according to some embodiments of the present invention.
Figure 1D:
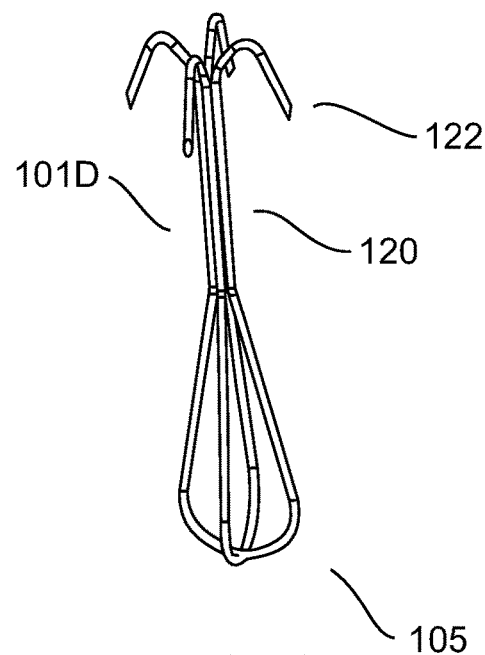
FIG. 1D is an illustration of a biodegradable blood vessel narrowing device with multiple anchoring legs in a closed state, according to some embodiments of the present invention.

FIGS. 1C and 1D illustrate a biodegradable blood vessel narrowing device 105 with multiple anchoring legs 120 in an open state 101C and a closed state 101D, according to some embodiments of the present invention. The biodegradable blood vessel narrowing device 105 illustrated in FIGS. 1C and 1D is a variation of the biodegradable blood vessel narrowing device 105 depicted in FIGS. 1A and 1B respectively. One aspect of this correspondence is that the anchoring legs 120 are spread apart in the open state 101C and in the twisted state 101A. In these states 101A, 101C the anchoring legs 120 can touch opposing sides of a blood vessel wall. In this example the anchoring legs 120 are spread apart by a biodegradable element 110. The anchoring legs 120 encircle the biodegradable element 110. Optionally, no retention element is required to hold the biodegradable element 110 between the anchoring legs 110. Optionally, the biodegradable element 110 contains one or more non degradable parts and/or a hollow chamber. The tendency of the anchoring legs to be in a closed configuration 101D may apply physical pressure towards the biodegradable element 110. In this example the biodegradable element 110 is shaped as a tube.

Figure 2A:
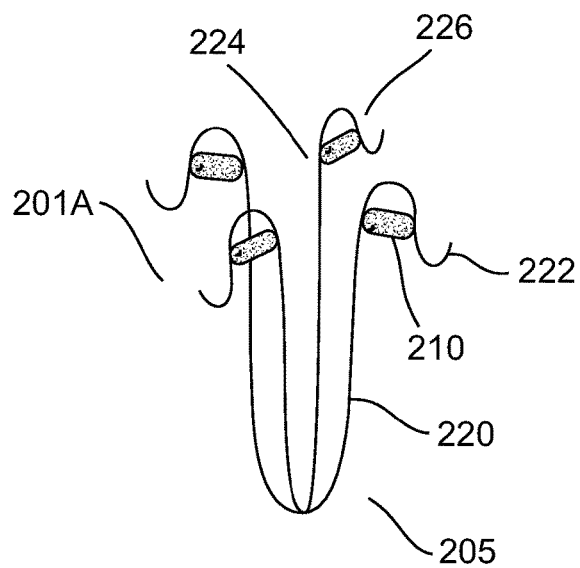
FIG. 2A is an illustration of a biodegradable blood vessel narrowing device with multiple anchoring legs having a biodegradable element between their first and second parts in a pre-degradation state, according to some embodiments of the present invention.
Figure 2B:
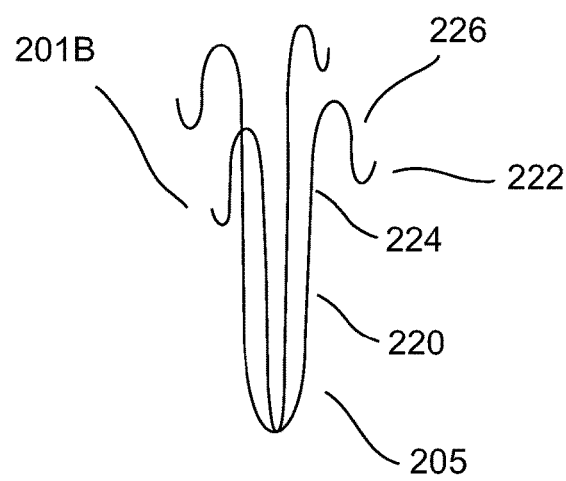
FIG. 2B is an illustration of a biodegradable blood vessel narrowing device with multiple anchoring legs having a biodegradable element between their first and second parts in a degraded state, according to some embodiments of the present invention.

FIGS. 2A and 2B illustrate a biodegradable blood vessel narrowing device 205 with multiple anchoring legs 220 having a biodegradable element between their first 224 and second parts 226, according to some embodiments of the present invention. FIG. 2A illustrates an open state 201A of the anchoring legs 220. The biodegradable blood vessel narrowing device 105 illustrated in FIGS. 2A and 2B is a variation of the biodegradable blood vessel narrowing device 105 depicted in FIGS. 1A, 1C and 1B, 1D respectively. The biodegradable blood vessel narrowing device 105 illustrated in FIG. 1C has four anchoring legs 220. Each leg has a first part 224 and a second part 226. The second part 226 of the anchoring leg 220 carries an anchoring tooth 222. The anchoring teeth 222 anchor to the walls of a blood vessel. Optionally, anchoring of the anchoring teeth 222 to blood vessel walls is performed without penetrating a blood vessel wall. A biodegradable element 210 is located between the first part 224 and the second part 226 of the anchoring legs 220 in an open state 201A. Upon the degradation of the biodegradable element 210, the biodegradable element 210 external dimensions become smaller and the first 224 and second 226 parts of the anchoring legs 220 get closer to one another. The walls of a blood vessel are pulled towards one another upon the degradation of the biodegradable element 210 as a result of the distance shortening between the first 224 and second 226 parts of the anchoring legs 220. Optionally, the change in the biodegradable element's 210 external dimensions is promoted by the shape memory of anchoring legs 120 made of SMA.

Figure 2C:
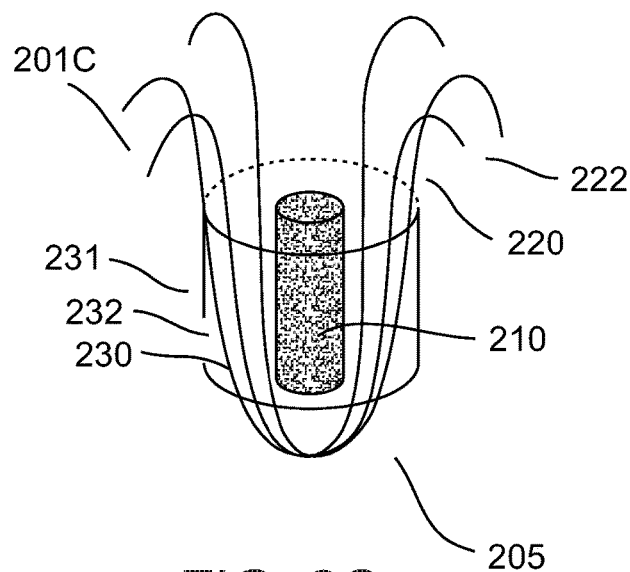
FIG. 2C is an illustration of a biodegradable blood vessel narrowing device with an encircling constriction element with an internal biodegradable element in an open state, according to some embodiments of the present invention.
Figure 2D:
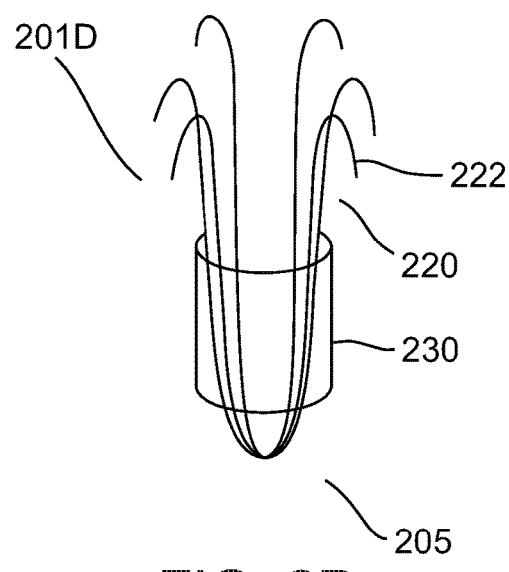
FIG. 2D is an illustration of a biodegradable blood vessel narrowing device with an encircling constriction element with an internal biodegradable element in a closed state, according to some embodiments of the present invention.

FIGS. 2C and 2D illustrate a biodegradable blood vessel narrowing device 205 with an encircling constriction element 230 with an internal biodegradable element 210 in an open state 201C and in a closed state 201D, according to some embodiments of the present invention. In the open state 201C the anchoring legs 220 are further apart from one another compared to the closed state 201D. The biodegradable blood vessel narrowing device 105 illustrated in FIGS. 2C and 2D is a variation of the biodegradable blood vessel narrowing device 105 depicted in FIGS. 1A, 1C, 2A and 1B, 1D, 2D respectively. In this example, the constriction element 230 encircles the anchoring legs 220. Optionally, the constriction element 230 encircles some of the anchoring legs 220. Optionally, the biodegradable blood vessel narrowing device 205 has multiple constriction elements 230. Each of the constriction elements 230 encircles a group of anchoring legs 220. Optionally, multiple constriction elements 230 may encircle the same anchoring legs 220, thereby creating an overlap between the groups of encircled anchoring legs 220. There is a biodegradable element 210 inside the constriction element 230. Optionally, the biodegradable element 210 is completely internal to the constriction element 230, having essentially no part of the biodegradable element 210 exposed to the blood. Optionally, the constriction element 230 is made of a non permeable material which does not enable the degraded parts of the biodegradable element 210 to pass from the internal side 231 of the constriction element 230 to its external side 232 which is exposed to the blood. Optionally, the biodegradable element 210 is located in the center of the constriction element 230. Optionally, the biodegradable element 210 is positioned symmetrically in respect to the shape of the constriction element 230 in order to promote symmetric narrowing of blood vessel walls. Optionally, the biodegradable blood vessel narrowing device 205 is removed the blood vessel after the blood vessel is narrowed. Optionally, drugs affecting the blood vessel diameter are provided prior to, along with and/or after inserting and/or deploying the biodegradable blood vessel narrowing device 205.

FIGS. 3A and 3B illustrate a biodegradable blood vessel narrowing device 305 with spring shaped anchoring legs 320A, 320B, according to some embodiments of the present invention. In this example there are two anchoring legs 320A, 320B, each shaped as a spring. Each of the spring shaped anchoring legs 320A, 320B has anchoring teeth 322. The anchoring teeth 322 anchor the biodegradable blood vessel narrowing device 305 to a blood vessel wall 340. A biodegradable element 310 spreads the spring shaped anchoring legs 320A, 320B apart to create an open state 301A. The spring shaped anchoring legs 320A, 320B tend to contract and wrap back together in a closed state 301B. The spring shaped anchoring legs 320A, 320B apply pressure on the biodegradable element 310. Upon degradation of the biodegradable element 310 the spring shaped anchoring legs 320A, 320B move towards one another creating a closed state 301B. In the closed state 301B the distance between the spring shaped anchoring legs 320A, 320B is reduced. The movement of the spring shaped anchoring legs 320A, 320B pulls the blood vessel walls toward each other which in turn narrow the blood vessel. Optionally, the spring shaped anchoring legs 320A, 320B is made of a shape memory alloy SMA comprising: copper-aluminium-nickel, nickel-titanium, zinc alloy, copper alloy, gold alloy and/or iron alloy. Optionally, a retention element maintains the position of the biodegradable element 310 with respect to the spring shaped anchoring legs 320A, 320B. Optionally, the biodegradable blood vessel narrowing device 305 has more than two anchoring legs 320A, 320B. Optionally, the plurality of spring shaped anchoring legs is organized in groups of anchoring legs.

FIGS. 4A and 4B illustrate a biodegradable blood vessel narrowing device 405 with an occlusion element 450, according to some embodiments of the present invention. The biodegradable blood vessel narrowing device 405 illustrated in FIGS. 4A and 4B is a variation over the biodegradable blood vessel narrowing device 105 depicted in FIGS. 1A, 1C and 1B, 1D respectively. In this example, there are no anchoring legs. The biodegradable element 410 carries an anchoring element such as anchoring teeth 422. When the biodegradable element 410 degrades the blood vessel walls are pulled therealong, narrowing the blood vessel. Optionally, the occlusion element 450 is attached to the biodegradable blood vessel narrowing device 405. Optionally, the attached occlusion element is anchored to the blood vessel walls along with the biodegradable blood vessel narrowing device 405. Optionally, the occlusion element 450 has a second anchoring element, such as anchoring teeth 452. Optionally, the biodegradable blood vessel narrowing device 405 occludes a blood vessel even without the occlusion element 450, and the occlusion element 450 supplies an additional safety net for complete and/or immediate occlusion of a blood vessel. The biodegradable blood vessel narrowing device 405 narrows the blood vessel walls 340, 540, 640, 840 to fit the device's 405 own dimensions, thereby occluding the blood vessel.

Figure 5A:
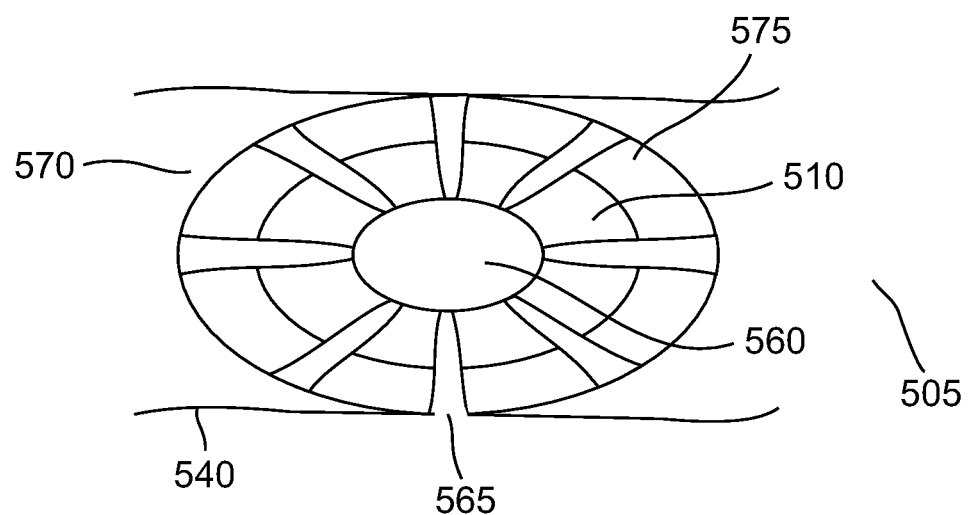
FIG. 5A is an illustration of a biodegradable blood vessel narrowing device with a glue chamber in a pre-degradation state, according to some embodiments of the present invention.
Figure 5B:
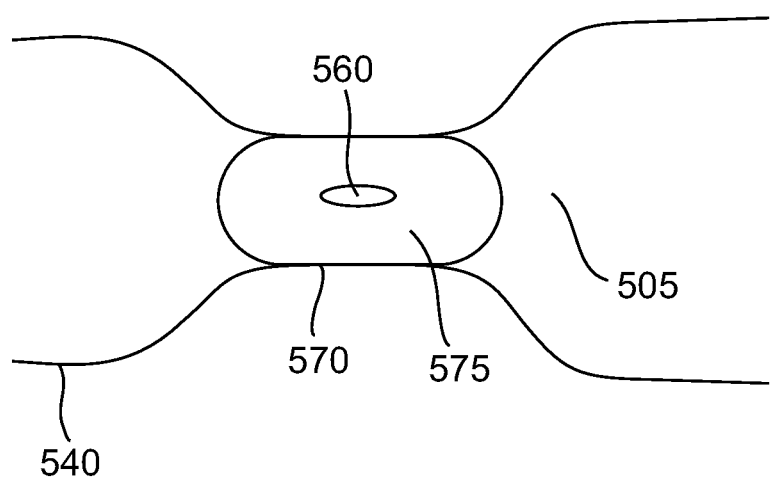
FIG. 5B is an illustration of a biodegradable blood vessel narrowing device with a glue chamber in a degraded state, according to some embodiments of the present invention.

FIGS. 5A and 5B illustrate a biodegradable blood vessel narrowing device 505 with a glue chamber, according to some embodiments of the present invention. The biodegradable blood vessel narrowing device 505 has a glue chamber 560 and a biodegradable element 510. The glue chamber 560 may be internal to the biodegradable element 510 as illustrated. Glue channels 565 connect the glue chamber 560 with the outer surface 570 of the biodegradable blood vessel narrowing device 505. The biocompatible glue passes through the glue channels 565. The bio-compatible glue reaches the outer surface 570 of the biodegradable blood vessel narrowing device 505. The bio-compatible glue glues the device 505 to a blood vessel wall after the device 505 deployment in a blood vessel. The biodegradable blood vessel narrowing device 505 is depicted here in two states: with a glue chamber 560 full of biocompatible glue and a biodegradable element 510 as illustrated in FIG. 5A and with a glue chamber 560 essentially empty of biocompatible glue and a degraded biodegradable element 510 as illustrated in FIG. 5B. Optionally, the biodegradable blood vessel narrowing device 505 is capsule shaped. Optionally, the biodegradable blood vessel narrowing device 505 has multiple glue chambers 560. Multiple glue chambers 560 may enable to reduce the distance between the glue chamber 560 and the outer surface 570, thereby reducing the force needed to inject the bio-compatible glue through the glue channels 565 and/or the distance and/or time the glue has to pass before sticking to a blood vessel wall 540. These may reduce the chances of a glue channel 565 block occurrence. Optionally, the biocompatible glue is released by applying external pressure onto the device 505.

Optionally, the biocompatible glue is released by injecting a second material into the glue chamber 560. The increase in fluid pressure forces the biocompatible into the glue channels 565. The second material, which is optionally inserted into the glue chamber 560, may be a fast bio-absorbable such as water, the patient's own blood etc. Optionally, the glue is released as a result of the pressure applied by the blood vessel walls on the biodegradable blood vessel narrowing device 505. Optionally, the glue release is dependent on degradation of the biodegradable element 510 and/or on absorption of a bio-absorbable material. Optionally, a layer 575 is external to the biodegradable element 510. The additional layer 575 may be made of a biocompatible polymer, a biocompatible material and/or an SMA. Upon degradation of the biodegradable element 510, the biodegradable element 510 essentially collapses towards the glue chamber. As a result the biocompatible polymer 575 shrinks and creates pressure towards the glue chamber, thereby releasing the bio-compatible glue. The biocompatible polymer layer 575 may be partial or essentially completely cover the biodegradable element 510. Optionally, a bio-absorbable element may function in a similar to the biodegradable element with respect to the bio-compatible glue release. Using a bio-absorbable element instead, in combination with and/or in addition to a biodegradable element 510 may reduce the glue release time. Optionally, the glue is not present in the glue chamber 560 at the time of device 505 deployment. The biocompatible glue may be inserted into the glue chamber 560 once the device 505 is in a blood vessel in a similar manner to that illustrated in FIGS. 6A-6C. The glue may be inserted to the device 505 through the glue channels and/or through a different opening.

FIGS. 6A, 6B and 6C illustrate a biodegradable blood vessel narrowing device 605 with an internal chamber 668 and a channel 685, according to some embodiments of the present invention. When the biodegradable blood vessel narrowing device 605 is deployed in a blood vessel the internal chamber 668 is typically empty. Once the device 605 is deployed a biocompatible material is inserted through the channel 685. The channel 685 connects the internal chamber 668 with the surface 670 of the device 605. The channel may penetrate the degradable element 610. Optionally, another layer 675 of material may essentially encircle the biocompatible element 610. This layer may also be made of a biodegradable material, an SMA and/or a biocompatible polymer. The additional layer 675 may apply pressure on internal layers promoting their degradation, shape modification and/or insertion into channel, as illustrated in FIGS. 5A-5B by the additional layer 575. Optionally, the degradable element 610 has a hollow tube which fits channel 685. Optionally, the channel 685 extends beyond the surface 670 of the device. Optionally, the channel 685 is inserted after deployment. The biocompatible material may be a bio-absorbable material such as water and/or other biocompatible absorbable materials and/or a biodegradable material such as collagen and/or biodegradable materials as listed above in FIGS. 1A and 1B. The operator inserts biocompatible material into the internal chamber 468 until the surface of the device 605 anchors to the blood vessel walls 640. Optionally, the device 605 contains an occlusion agent for occluding the blood vessel. The occlusion may be complete and/or partial, i.e. some of the blood streaming through the blood vessel is blocked and some of the blood still flows through the blood vessel with the partially occluding device 605. Optionally, more biocompatible material is inserted to create pressure on the blood vessel walls. Optionally, monitoring means such as a camera and/or a pressure detector are used to determine when to stop the biocompatible material insertion. Optionally, once the biocompatible material is contained in the internal chamber 668 the channel 685 is removed. When the biocompatible material and/or the biodegradable element 610 the blood vessel walls which are anchored to the device 610 are pulled inward, thereby narrowing the blood vessel. Optionally, the biocompatible material in the internal chamber 668 is absorbed and/or degraded in a different pace compared to the degradation pace of the biodegradable element 610.

Figure 7:
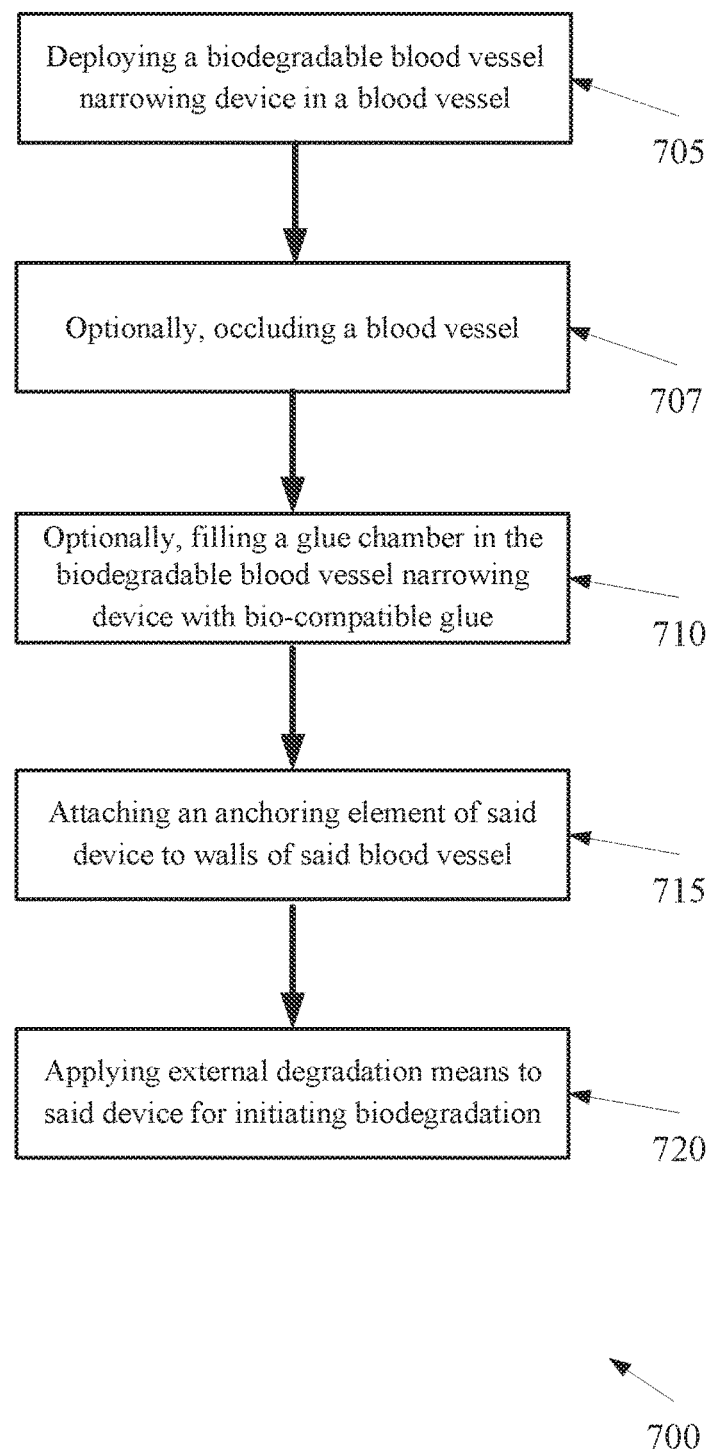
FIG. 7 is a flowchart of a method 700 for narrowing a blood vessel, according to some embodiments of the present invention.

Reference is now also made to FIG. 7 which is a flowchart of a method 700 for narrowing a blood vessel, according to some embodiments of the present invention. First, a biodegradable blood vessel narrowing device is deployed in a blood vessel 705. Optionally, the blood vessel is occluded 707. The occlusion may be performed by the biodegradable blood vessel narrowing device 105, 205, 305, 405, 505 and/or 605. Optionally, the occlusion is performed by an independent occlusion device. Optionally, the deployed biodegradable blood vessel narrowing device is one of the variations illustrated in FIGS. 1A-6C and/or a combination thereof. Then, optionally, glue chamber is filled in the biodegradable blood vessel narrowing device is filled with bio-compatible glue 710. Then, an anchoring element of said biodegradable blood vessel narrowing device is attached to the blood vessel walls 715. The attachment may be performed by hooks, by biocompatible glue and/or other anchoring means. The anchoring element may attach to the blood vessel wall by itself upon deployment. For example, hooks on anchoring legs that are in close proximity to a blood vessel walls. Optionally, the device 105, 205, 305, 405, 505 and/or 605 is moved in the blood vessel to facilitate the attachment of the anchoring element to the blood vessel walls. Optionally, external means are applied to facilitate the attachment of the anchoring element to the blood vessel walls such as applying pressure on tissue around blood vessel. Optionally, a chamber in the biodegradable blood vessel narrowing device is filled with a bio-absorbable material. The filling of a chamber in the biodegradable blood vessel narrowing device with a bio-absorbable may be performed as illustrated in FIG. 6B. The bio-absorbable material fill may promote the anchoring of the device to the blood vessel walls by bringing the blood vessel walls and the anchoring means closer together. Then, optionally, external degradation means are applied to the biodegradable blood vessel narrowing device for initiating biodegradation 720. External degradation means may be selected from: external pressure, light emission, sound waves, degradation promoting agent, chemical compound delivery and/or a laser beam. Optionally, a chamber in said device is filled with a bio-absorbable material.

Reference is now also made to FIG. 8 which illustrates a blood clot cage 890, according to some embodiments of the present invention. The blood clot cage is depicted here deployed in a blood vessel 840. The blood vessel 840 has a front 840A and a rear side 840B as defined by the blood flow which occurs from the rear side 840B to the front side 840A. The blood clot cage 890 may be positioned in front of the biodegradable narrowing device. The blood clot cage 890 assists in catching a blood clot that may be formed as a result of the blood vessel occlusion.

It is expected that during the life of a patent maturing from this application many relevant SMA, biocompatible glues, bio-absorbable materials, biocompatible polymers, external degradation means, anchoring means will be developed and the scope of the terms SMA, biocompatible glue, bio-absorbable material, biocompatible polymer, external degradation mean, and/or anchoring mean are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A biodegradable blood vessel narrowing device, comprising:
    a biodegradable element;
    an anchoring element sized and shaped to be anchored to a blood vessel wall when located in a blood vessel lumen and being in an open state, wherein the anchoring element comprises a plurality of anchoring legs; each of the anchoring legs having at least one anchoring tooth configured to anchor to the blood vessel wall and wherein a distance between at least two respective anchoring teeth shortens upon degradation of the biodegradable element, the plurality of anchoring legs encircling the biodegradable element;
    wherein a constriction element is configured to encircle the plurality of anchoring legs and the biodegradable element is positioned inside the constriction element and upon degradation of the biodegradable element the constriction element applies pressure on the plurality of anchoring legs thereby pulling the plurality of anchoring legs;
    wherein at least one external dimension of the biodegradable element is reduced upon degradation of the biodegradable element thereby transitioning the anchoring element from the open state to a closed state;
    wherein the anchoring element pulls the blood vessel walls inwardly toward one another by the transitioning;
    wherein the constriction element encircles the plurality of anchoring legs in both the open state and the closed state.

2. The device of claim 1, wherein the anchoring element is made of a shape memory alloy (SMA).

3. The device of claim 1, wherein the anchoring element is made of a biocompatible polymer.

4. The device of claim 1, wherein the device occludes a blood vessel upon the device deployment in the blood vessel.

5. The device of claim 1, wherein the device is configured to partially occlude a blood vessel upon the device deployment in the blood vessel.

6. The device of claim 1, wherein a degradation of the biodegradable element is initiated by external degradation means.

7. The device of claim 6, wherein the external degradation means is one of at least an external pressure, light emission, sound waves, a degradation promoting agent, a chemical compound delivery and a laser beam.

8. The device of claim 1, wherein the constriction element is made of a non-permeable material that does not enable degraded parts of the biodegradable element to pass from an internal side of the constriction element, which is exposed to the biodegradable element, to an external side of the constriction element, which is exposed to the blood vessel lumen.

9. The device of claim 1, wherein, in the open state, the biodegradable element is positioned symmetrically in respect to a shape of the constriction element in order to promote symmetric narrowing of the blood vessel walls.

10. A method for occluding and narrowing a blood vessel, comprising:
    deploying a biodegradable blood vessel narrowing device having an anchoring element in a blood vessel;
    wherein narrowing of the blood vessel is mechanically linked to degradation of the biodegradable blood vessel narrowing device;
    wherein the anchoring element is sized and shaped to be anchored to a blood vessel wall when located in a blood vessel lumen and being in an open state, wherein the anchoring element comprises a plurality of anchoring legs; each of the anchoring legs having at least one anchoring tooth configured to anchor to the blood vessel wall and wherein a distance between at least two of respective the anchoring teeth shortens upon degradation of the biodegradable element, the plurality of anchoring legs encircling the biodegradable element;
    wherein the biodegradable blood vessel narrowing device comprises a constriction element wherein the constriction element encircles the plurality of anchoring legs and the biodegradable element is positioned inside the constriction element and upon degradation of the biodegradable element the constriction element applies pressure on the plurality of anchoring legs thereby pulling the plurality of anchoring legs;
    wherein at least one external dimension of the biodegradable element is reduced upon degradation of the biodegradable element thereby transitioning the anchoring element from the open state to a closed state, wherein the anchoring element pulls the blood vessel walls inwardly toward one another by the transitioning; and wherein the constriction element encircles the plurality of anchoring legs in both the open state and the closed state.

11. The method of claim 10, further comprising applying external degradation means to the device for initiating biodegradation.

12. The method of claim 10, wherein the constriction element is made of a non-permeable material that does not enable degraded parts of the biodegradable element to pass from an internal side of the constriction element, which is exposed to the biodegradable element, to an external side of the constriction element, which is exposed to the blood vessel lumen.

13. The method of claim 10, wherein, in the open state, the biodegradable element is positioned symmetrically in respect to a shape of the constriction element in order to promote symmetric narrowing of the blood vessel walls.

* * * * *